United States Patent [19]
Takahashi et al.

[11] Patent Number: 4,985,360
[45] Date of Patent: Jan. 15, 1991

[54] NOVEL BILIRUBIN OXIDASE WHICH HAS A SUBSTRATE SPECIFITY TO BILIRUBIN, BUT NOT TO BILIVERDIN, CATECHOL AND HEMIN

[75] Inventors: Mamoru Takahashi; Shigeyuki Imamura; Masaki Takada, all of Shizuoka, Japan

[73] Assignee: Toyo Jozo Kabushiki Kaisha, Shizuoka, Japan

[21] Appl. No.: 204,868

[22] Filed: Jun. 10, 1988

[30] Foreign Application Priority Data

Jun. 10, 1987 [JP] Japan ................... 62-144964

[51] Int. Cl.$^5$ .......................... C12N 9/02; C12N 1/00; C12N 1/14; C12Q 1/26
[52] U.S. Cl. ...................... 435/189; 435/25; 435/254; 435/933
[58] Field of Search ................ 435/25, 189, 254, 933

[56] References Cited

U.S. PATENT DOCUMENTS

| | | | |
|---|---|---|---|
| 4,211,844 | 7/1980 | Wu | 435/189 |
| 4,544,249 | 11/1985 | Kosaka et al. | 435/189 |
| 4,569,912 | 2/1986 | Matsui et al. | 435/189 |
| 4,571,383 | 2/1986 | Takayama et al. | 435/25 |
| 4,600,689 | 7/1986 | Matsui et al. | 435/189 |
| 4,677,062 | 6/1987 | Uwajima et al. | 435/189 |
| 4,770,997 | 9/1988 | Yoshino et al. | 435/189 |

FOREIGN PATENT DOCUMENTS 0005637 11/1979 European Pat. Off. .
0140004 5/1985 European Pat. Off. .

OTHER PUBLICATIONS

"Purification and Characterization of *Bacillus coagulans* oligo-1,6-glucosidase", *European Journal of Biochemistry*, vol. 158, 1986, by Y. Suzuki et al., p. 77–83.

*Primary Examiner*—Elizabeth C. Weimar
*Assistant Examiner*—Eric J. Kraus
*Attorney, Agent, or Firm*—Young & Thompson

[57] ABSTRACT

A novel bilirubin oxidase is provided having a substrate specificity for bilirubin but not to, at least, biliverdin, catechol and hemin and which catalyzes the enzyme reaction between two moles of bilirubin and one mole of oxygen to yield two moles of biliverdin and two moles of water. A process is also provided for the production of said novel bilirubin oxidase, which comprises cultivating a bilirubin oxidase-producing fungus of the genus Penicillium in a culture medium and collecting the bilirubin oxidase from the culture mixture. A method of determining the content of bilirubin in a sample to be analyzed is further provided which comprises contacting the sample with the bilirubin oxidase to convert bilirubin in the sample into biliverdin and determining the amount of biliverdin formed or the amount of oxygen consumed therefor, as well as a method for removing bilirubin contained in a sample to be analyzed, which comprises contacting the sample with said novel bilirubin oxidase.

7 Claims, 5 Drawing Sheets

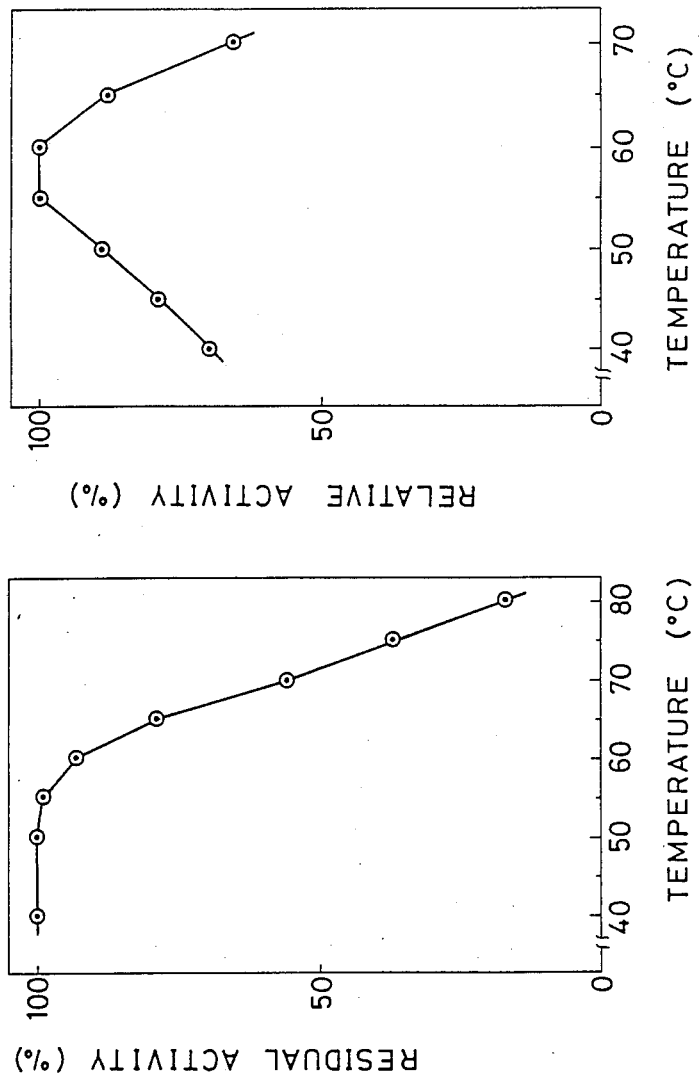

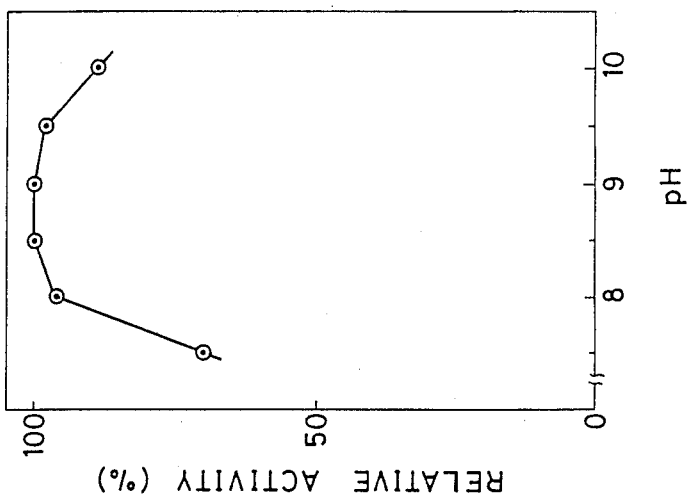
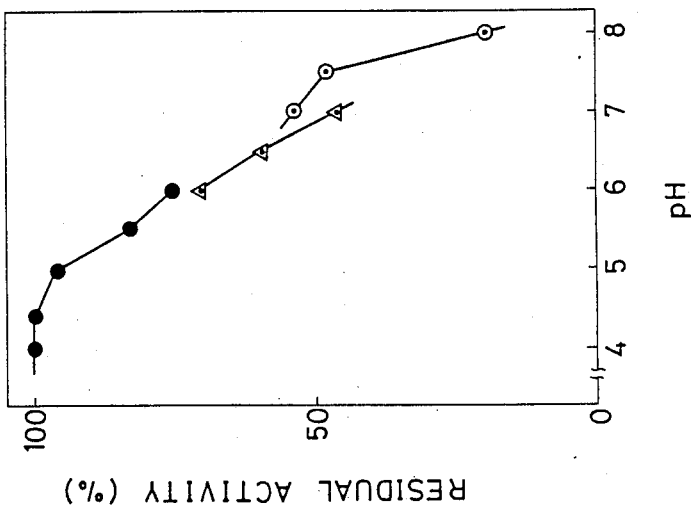

NOVEL BILIRUBIN OXIDASE WHICH HAS A SUBSTRATE SPECIFITY TO BILIRUBIN, BUT NOT TO BILIVERDIN, CATECHOL AND HEMIN

BACKGROUND OF THE PRESENT INVENTION

The present invention relates to a novel bilirubin oxidase, a process for its production and use thereof.

Bilirubin oxidase is an enzyme which catalyzes the reaction of two moles of bilirubin with one mole of oxygen yielding two moles of biliverdin and two moles of water. Various such enzymes have been reported, such as those derived from mycota of genus Myrocesium (Japanese Patent Application Laid Open No. 12032/1985), g. Bacillus (Japanese Patent Application Laid Open No. 209587/1986), g. Schizophyllum (Japanese Patent Application Laid Open No. 135886/1984), g. Coprinus, g. Trametes, g. Choriolama, g. Pholiota, g. Pleurotus, g. Rendides and g. Fusidopsis (Japanese Patent Application Laid Open No. 198971/1984) and from plantae of families Solanaceae, Musaceae and Liliaceae (Japanese Patent Application Laid Open No. 78580/1985) and so on.

Bilirubin is a yellow substance formed in blood by the decomposition of hemoglobin and constitutes a principal pigment of bile produced in liver. In blood serum, bilirubin exists in both conjugated and free forms. When the amount of conjugated bilirubin increases in blood serum, a dysfunction of the bilirubin transport system to the duodenum may occur by conjugation in the liver microsome and, if the amount of free bilirubin becomes excessive, a hemolytic anemia etc. will occur. Therefore, the ability to analytically quantify both the conjugated and the free bilirubin is clinically very important.

With respect thereto, bilirubin oxidase is also very useful for intentionally decreasing the bilirubin level in a sample to be analyzed.

Known bilirubin oxidases as mentioned above have low substrate specificity, so that their application in the field of, such as, clinical chemistry has not been without problem. Thus, all known bilirubin oxidases derived from microorganisms exhibit a substrate specificity to biliverdin, so that they are not suitable for quantitative analysis of bilirubin. On the other hand, the enzymes derived from plants suffer from restriction with regard to availability due to seasonal limitation, which is disadvantageous for industrial production, as well as with respect to a difference in the degree of substrate specificity exhibited for each specific enzyme. For example, it is suggested in the patent literature that the enzyme obtained from Solanaceae has no effect on biliverdin and hemoglobin. Known bilirubin oxidases act on substances having the tetrapyrrole structure and on phenolic substances. Therefore, the action of these oxidases would be considerably influenced by the presence of foreign substances, if employed for the biochemical examination of blood during clinical examination.

OBJECTS AND SUMMARY OF THE INVENTION

An object of the present invention is thus to provide a novel bilirubin oxidase in which the shortcomings of the prior art enzymes have been obviated and which has a substrate specificity to bilirubin but not to, at least, biliverdin, catechol and hemin and which catalyzes the enzyme reaction of two moles of bilirubin with one mole of oxygen to yield two moles of biliverdin and two moles of water.

The inventors had thus conducted a thorough investigation to find a bilirubin oxidase which does not exhibit such defects and have accordingly identified a strain of fungus identified by the denotation M 5613 which belongs to imperfect fungi and which has been isolated from a soil in Nagaizumi-cho, Sunto-gun, Shizuoka Prefecture, Japan which produced a bilirubin oxidase catalyzing the enzyme reaction of bilirubin with oxygen forming biliverdin and water. This bilirubin oxidase surprisingly exhibits a substrate specificity to bilirubin but not to biliverdin, catechol and hemin.

A process is also provided for the production of said bilirubin oxidase which comprises cultivating a bilirubin oxidase-producing fungus of the genus Penicillium in a culture medium and collecting the bilirubin oxidase from the culture medium.

A method of use of said bilirubin oxidase is also provided wherein said bilirubin oxidase is used for a quantitative determination of bilirubin in a sample to be analyzed.

Additionally, the bilirubin oxidase may be utilized for intentionally eliminating the content of bilirubin in a sample to be analyzed for substances other than bilirubin.

BRIEF DESCRIPTION OF THE DRAWINGS

FIG. 1 is a graph showing the heat stability of the bilirubin oxidase according to the present invention.

FIG. 2 is a graph showing the optimum activity in relation to temperature of the bilirubin oxidase according to the present invention.

FIG. 3 is a graph relating activity to pH range of the bilirubin oxidase according to the present invention.

FIG. 4 is a graph relating activity to optimum pH of the bilirubin oxidase according to the present invention.

DETAILED DESCRIPTION OF THE PRESENT INVENTION

Figure 5:
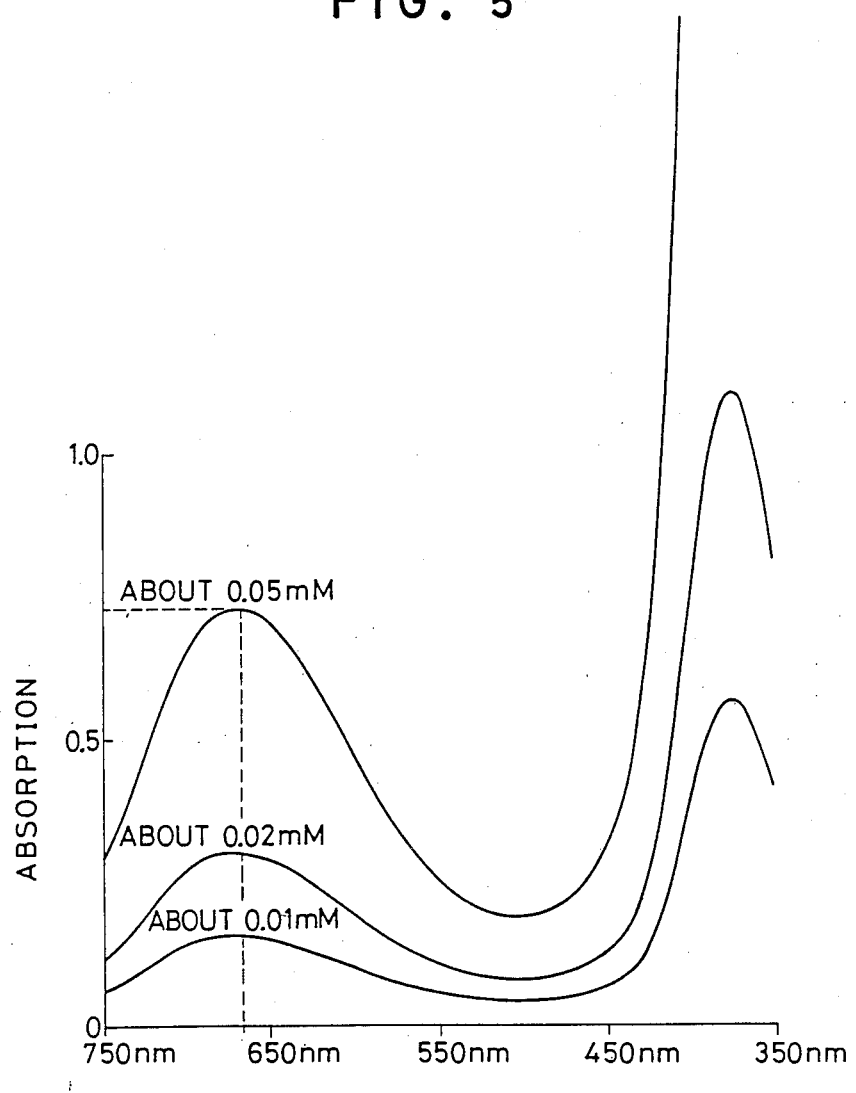
FIG. 5 depicts an absorption spectrum of a biliverdin solution of the present invention.

The taxonomical characteristics of the novel bilirubin oxidase-producing fungus according to the present invention are as follows:

(1) State of Growth in Various Culture Media (a) In Czapek Agar Medium ($C_2$)

At 25° C., the growth is ordinary and forms a flat wooly fibrous colony having a diameter of 36–40 mm after 7 days. It has a color of pale yellow (Methuen 3A3), emits only a small amount of colorless exudate or possibly no exudate and produces no dispersing pigment. The bottom face is grayish yellow (4C5).

(b) In a Yeast Extract-Containing Czapek Agar Medium (CYA)

At 25° C., the growth is prompt and forms a somewhat thicker wooly fibrous colony having a diameter of 45–49 mm after 7 days. It has 4–5 lines of wrinkles and exhibits a mixture of pale red (9A3) and greenish gray (27A3) colors with a green periphery. The exudate is in the form of a large pale red (9A3) droplet. The bottom face is violet brown (11E8).

(c) In a Malt Extract Agar Medium (HA)

At 25° C., the growth is prompt and forms a flat wooly fibrous colony having a diameter of 48–51 mm after 7 days. It is grayish green (29C3) with a green periphery. No emission of exudate nor dispersing pigment exists. The bottom face is olive brown (4D7).

(2) Physiological Properties

| Growth permitting pH range | from 1.5 to 10.5 |
| Optimum pH | 3.5–8.5 |
| Growth permitting temperature range | from 17 to 37° C. |
| Optimum growing temperature | 28–34° C. |

(3) Morphic Characteristics under Microscope

No sexual generation is recognizable and multiplication occurs by conidiospore. The conidiospore comes from substrate hypha or from aerial hypha and is relatively long with a size of 100–250×2.5–2.8 μm and with a smooth or a little rough wall surface. The manner of formation of the conidium is in a type of phialophora. A peniculus is from monoverticillate to diraricate. The metula diverges at a wide angle with a size of 11–15×2-.5–2.8μm in 2–3 verticils. The phialide is in an ampulliform with a size of 7–10×2–2.5 μm in 4–7 verticils. The conidium is nearly spherica ellipsoidal with a little inclusion of pear-formed ones and has a size of 2.3–3.0×2-.0–2.5 μm with a smooth or a little rough wall surface.

Because of the formation of an exogeneous conidium, the strain M 5613 was judged to fall under the Deuteromycotina. Since the mode of formation of conidium is a type of phialophora and the conidium shoots from the top of the phialide, this strain belongs to the genus Penicillium. Therefore, reference is made to the literature "The Genus Penicillium", Academic Press, London, p. 434 (1979) and "A Manual of the Penicillia", The Williams & Wilkins, Baltimore, p. 875 (1949). And, since a peniculus is in monoverticillate to diraricate and grows promptly in culture media and exhibits a characteristic feature of violet brown bottom face in CAY and so on, species coming into consideration as corresponding to M 5613 are *Penicillium janthinellum* and *Penicillium simplicissimum*. *Pencillium simplicissimum* has a long conidiophore of some 400–800 μm with a rough wall surface thereof and exhibits no violet brown bottom face, so that it was able to be distinguished. Thus, the strain M 5613 was identified to be *Penicillium janthinellum*.

The denotation of the color of the colony was made in accordance with the Code of Denotation of Kornerup, A. and J. H. Wanscher; "Methuen Handbook of Color", 3rd ed. (1978), Eyre Methuen, London.

The strain of fungus according to the present invention has been deposited at the Institute of Microbiological Industry and Technology of the Agency of Industrial Science and Technology Japan by the denotation "Penicillium janthinellum M 5613" under deposition No. Bikoken-joki 1674 (FERM BP-1674).

For producing the bilirubin oxidase according to the present invention, the bilirubin oxidase-producing fungus is cultivated by the usual technique for producing enzymes. The cultivation may be effected either in liquid phase or in solid phase, and it is advantageous for an industrial process to undertake the cultivation by inoculating the cells of said fungus in a culture medium by a deep aeration cultivation with agitation.

With regard to the composition of the culture medium used to cultivate the bilirubin oxidase-producing fungus, those which are usually used for cultivating the fungi of Penicillium can be employed. As the nitrogen source, any nitrogen compound capable of being utilized as a nitrogen source can be used, for example, corn steep liquor, peptone, casein, soybean powder, yeast extract and meat extract of various origins. As the carbon source, every nutritive carbon compound may be used, for example, molasses, glucose, sucrose, dextrine and so on. Potato extract is also a suitable component of the culture medium. Inorganic salts, such as, sodium chloride, potassium chloride, magnesium sulfate, potassium dihydrogen phosphate, potassium monohydrogen phosphate and so on, may also be added as required.

The cultivation temperature may be modified within the permissible range for the growth of the fungus and for the production of bilirubin oxidase and may, in general, range from 20° to 37° C., preferably from 25° to 30° C., most preferably about 28° C. The time for cultivation may differ in accordance with each specific culture condition and may range from 2–8 days and, in particular, about 4 days. It is natural, however, to terminate the cultivation over an adequate time interval, by observing the titer of the bilirubin oxidase to detect the maximum point.

After the cultivation, the enzyme according to the present invention can be recovered from the cultivation mixture by employing usual techniques for collecting enzymes. The bilirubin oxidase according to the present invention exists both in the culture liquid phase and in the interior of the cell. While the enzyme according to the present invention is usually collected from the culture liquid phase after removal of the fungus cells from the culture liquid, it is possible also, considering the collection efficiency etc., to additionally collect the enzyme in the interior of the cell by usual techniques for collecting enzymes from cell interiors, in order to collect both portions of enzymes.

The crude enzyme solution obtained in this manner may be subjected to a refining step in a known manner for isolating and purifying proteins and enzymes, in order to obtain the purified bilirubin oxidase. There may be employed, or example, a technique of fractional precipitation by adding to the crude solution of bilirubin oxidase an organic solvent, such as, acetone, methanol and so on, or a salting-out technique by adding to the crude solution an inorganic salt, such as ammonium sulfate, sodium chloride, aluminum sulfate and so on, in order to fractionally precipitate the enzyme.

To accomplish additional purification which may be required occasionally, the collected precipitate is dissolved again in an adequate solvent, such as a tris-hydrochloric acid buffer solution and the solution subjected to a purification treatment by, for example, a combination of adsorption chromatographies on a gel filtrant or on an ion exchange resin, such as, carboxymethyl-cellulose, carboxymethyl-dextran gel, sulfopropyl-dextran gel and polyacrylamide gel, whereupon the so treated product is dried (e.g., by freeze-drying) to obtain a highly purified product.

The physiochemical properties of the so obtained bilirubin oxidase according to the present invention are given below.

I. METHOD OF DETERMINING THE ENZYME ACTIVITY

Preparation of the Substrate Solution 6 mg of a non-conjugated and non-combined bilirubin obtained from the Japanese firm Wako Junyaku are placed in a beaker and are wetted with 0.5 ml of 5 N NaOH solution. Thereto are added 10 ml of 1M trishydrochloric acid Buffer (pH 8.5) under agitation while adding thereto 70 ml of water. The pH thereof is adjusted to 8.4, whereupon the solution is increased to 100 ml with water.

Preparation of the Enzyme Solution 50 mg of a freeze-dried product of bilirubin oxidase, which is obtained by the procedures given in Example 5, are weighed and dissolved in 65 ml of distilled water, whereupon the temperature thereof is adjusted to 37° C.

Determination of the Enzyme Activity 3 ml of the substrate solution are placed in a small test tube and let stand for 2 minutes in a water bath at 37° C., whereupon the reaction is commenced by adding 0.1 ml of the enzyme solution. After the reaction has been effected at 37° C. for exactly 10 minutes, an absorbancy at 680 nm of the reaction solution (absorbancy=$A_1$) is determined using a spectrophotometer. As the control test, the same absorbancy measurement is carried out for a solution prepared by adding 0.1 ml of water, instead of adding 0.1 ml of the enzyme solution, to the substrate solution (absorbancy=$A_2$).

The bilirubin oxidase activity (U/ml) is calculated by the equation $$U = \frac{A_1 - A_2}{10 \text{ min.}} \times \frac{1}{11.9} \times \frac{3.1}{0.1}$$

The arithmetic coefficient 11.9 in the above equation corresponds to the light absorbancy of 1 mM solution of biliverdin at 680 nm. For this, 8.3 mg of a commercial product of biliverdin dihydrochloride (Lot No. 43F-8020 of the firm Sigma) were dissolved in 10 ml of 1M trishydrochloric acid buffer and 70 ml of water added, whereupon the pH was adjusted to 8.4 using 5 N NaOH solution and increased to 100 ml with water. This solution was diluted with 0.1M tris-hydrochloric acid buffer solution of pH 8.4 to a volume of either 2, 5 or 10 times of its original volume, respectively, to prepare 3 dilute solutions and the total absorbancy in the wave length range from 750 to 350 nm for each solution determined using a spectrophotometer (Model UV-210A of the Japanese firm Shimadzu Corporation). As shown in FIG. 5, the light absorbancy at 680 nm for the biliverdin solution diluted to two times volume was found to be 0.73, that for the solution diluted to five times volume to be 0.30 and that for the solution diluted to ten times volume to be 0.155. From these results, the absorbancy at 680 nm of 1 mM solution of biliverdin was estimated to be 11.9.

II. SUBSTRATE SPECIFICITY

The intrinsic substrate specificity for various substrates was estimated based upon the oxygen consumption rate using an electrode oxygen meter. The measurements were effected under an addition of $HgCl_2$ to the substrate solution up to a concentration of 0.1 mM. For the measurements, 0.1 mM solution of the substrate with addition of 0.1 ml of the enzyme solution as employed in the determination of the enzyme activity was used. Results are as given in Table 1, wherefrom it is clear that all substrates other than bilirubin did not undergo any sign of reaction. Thus, it was confirmed that the bilirubin oxidase according to the present invention has a very high specificity to bilirubin.

TABLE 1

| Substrate Specificity | |
|---|---|
| Substrate | Relative Activity (%) |
| Bilirubin | 100 |
| Biliverdin | 0 |
| Pyrogallol | 0 |
| Catechol | 0 |
| Chlorophyllin | 0 |
| Chlorophyll | 0 |
| Hemoglobin | 0 |
| Hemin | 0 |
| Hematoporphyrin | 0 |
| Phenol | 0 |
| 4-Aminoantipyrin | 0 |
| Vitamin $B_{12}$ | 0 |
| Hydroquinone | 0 |

III. ENZYME ACTION

The enzyme catalyses the reaction:

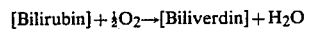

$$[\text{Bilirubin}] + \tfrac{1}{2}O_2 \rightarrow [\text{Biliverdin}] + H_2O$$

IV. HEAT STABILITY

To 0.5 ml of 0.2M of a buffer solution (pH 6.5) of potassium salt of phosphate, 0.5 ml of the above-mentioned enzyme solution is added and the resulting solution heated to each predetermined temperature between 40° and 80° C. for 30 minutes, whereupon the remaining enzyme activity is determined by the enzyme activity determination procedures described previously. The results obtained are as shown in FIG. 1, indicating that the solution was stable at temperatures up to 50° C.

V. OPTIMUM TEMPERATURE

Using the substrate solution employed in the determination of enzyme activity, the enzyme activity of the bilirubin oxidase according to the present invention is determined at predetermined temperatures between 40° and 70° C., the results of which are as shown in FIG. 2, indicating that the optimum temperature lay between 55°-60° C.

VI. STABLE PH RANGE

To 0.5 ml of the above-mentioned enzyme solution, there is added 0.5 ml of various pH-buffer solutions in a concentration of 0.2M and the resulting solution is heated at 70° C. for 30 minutes. Using 0.1 ml of the enzyme solution, the remaining enzyme activity was determined by the procedures of the enzyme activity determination given above to evaluate the influence of pH. The results obtained are as shown in FIG. 3, in which the curve ●—● represents the case where an acetic acid buffer solution (pH 4–6) was employed, the curve △—△ denotes the case where a potassium phosphate buffer solution (pH 6–7) was used and the curve ○—○ shows the case where a tris-hydrochloric acid buffer solution (pH 7–8) was employed. It was observed that the stable pH range for the bilirubin oxidase according to the present invention was at a pH of 4.0–4.5.

VII. OPTIMUM PH

The substrate solution prepared by the procedures for the enzyme activity determination was subjected to a pH-adjustment to one of the pH values of 7.5, 8.0, 8.5, 9.0, 9.5 and 10 by use of 5 N HCl solution and 5 N NaOH solution. The optimum pH was determined using these solutions. Here, it was assumed that the absorbancy of biliverdin will not vary with the variation in the pH value. Results are shown in FIG. 4, indicating that the optimum pH lies at 8.5–9.0.

VIII. INHIBITION AND ACTIVATION

The enzyme activity of the bilirubin oxidase according to the present invention is determined in accordance with the enzyme activity measuring procedure under an addition of either a metal ion, EDTA or a surfactant in an amount of 1 mM, 1 mM or 0.05% respectively. The relative enzyme activity was determined assuming the activity without addition to be 100. The results obtained are given in Table 2, showing that the activity is accelerated considerably by mercuric ion, lead ion and cetyl trimethylammonium chloride and is inhibited by copper ion and cobalt ion.

TABLE 2

| | Relative Enzyme Activity | | |
|---|---|---|---|
| Additive Substance | Relative Acty. (%) | Additive Substance | Relative Acty. (%) |
| KCl | 106 | $CoCl_2$ | 0 |
| NaCl | 106 | $AlCl_3$ | 88 |
| LiCl | 112 | $FeCl_3$ | 113 |
| CsCl | 139 | Hydroxylamine | 108 |
| $NaN_3$ | 106 | Triazole | 105 |
| $NH_4Cl$ | 108 | EDTA | 102 |
| KCN | 99 | Pluronic L-71 | 102 |
| $MgCl_2$ | 96 | Adecatol NP-690 | 107 |
| $BaCl_2$ | 49 | Adecatol PC-8 | 152 |
| $CaCl_2$ | 31 | Niccole TL-10 | 129 |
| $ZnCl_2$ | 60 | Niccole TO-10 | 137 |
| $NiCl_2$ | 43 | Twin 80 | 114 |
| $MnCl_2$ | 10 | CTMC* | 316 |
| $HgCL_2$ | 1206 | CTMB** | 277 |
| $CuCL_2$ | 0 | Control | 100 |
| $PbCl_2$ | 377 | | |

*Cetyl trimethylammonium chloride
**Cetyl trimethylammonium bromide

IX. MOLECULAR WEIGHT

According to gel filtration technique using Sephadex G-200 and employing a molecular weight marker of catalase, ferritin and thyroglobulin, the molecular weight was determined to be 500,000±50,000.

X. ISOELECTRIC POINT

The isoelectric point was observed using a focusing electrophoresis apparatus, whereby an isoelectric point of pH 4.7±0.5 was obtained.

XI. KM VALUE

Each finite amount of 2, 4, 6, 8, 10, 14 or 20 mg of standard sample of bilirubin supplied from the firm Wako Junyaku was dissolved in accordance with the procedures for preparing the substrate solution described above for the determination of enzyme activity and the Km value was determined using 0.1 ml of the enzyme solution as in the determination of the enzyme activity, whereby a Km value of $1.1 \times 10^4$ was obtained for bilirubin under this condition.

Comparing the properties determined above with the known bilirubin oxidases, it was confirmed that the enzyme according to the present invention differs from all the known enzymes.

To determine the amount of bilirubin in a sample to be analyzed using the bilirubin oxidase according to the present invention, a known method for determining bilirubin can be used. Thus, the content of bilirubin in the sample to be analzyed is converted by the action of the bilirubin oxidase according to the present invention into biliverdin and the amount of the so formed biliverdin or the amount of oxygen consumed therefor may be employed to estimate the amount of bilirubin in the sample.

To determine the bilirubin content in a sample to be analyzed, the amount of bilirubin oxidase of the present invention to be added to the sample may be in the range from 0.01 to 10 units calculated as the bilirubin oxidase activity, among which an adequate amount may be chosen in accordance with the time required for the determination. It may be possible to add a reaction accelerator, such as, sodium dodecyl sulfate, sodium cholate, potassium ferricyanide; a buffer solution; a stabilizer for the enzyme and so on, as required.

The bilirubin oxidase of the present invention may also be employed to separately analyze the conjugated and non-conjugated bilirubins in a sample to be analyzed. For example, the conjugated bilirubin can be determined by analyzing by use of the enzyme of the present invention at a pH lower than 6 and the total bilirubin content can be determined by analyzing at a Ph of 6–10, so that the content of the non-conjugated bilirubin may be calculated by subtracting the amount of conjugated bilirubin from the amount of total bilirubin.

In addition, it is possible to intentionally remove bilirubin in a clinical examination sample for analyzing substances other than bilirubin, such as those samples used to analyze glucose using a system of glucose oxidase/peroxidase, to analyze cholesterol oxidase using a system of glucose cholesterol oxidase/peroxidase and so on, in which bilirubin acts as an inhibitor in the analysis reaction, by adding to the sample the bilirubin oxidase according to the present invention.

The invention will be further described by way of the following Examples, wherein it is to be noted that the scope of the invention should by no means be restricted only to such specific Examples but other alterations and modifications are possible without departing from the scope of the present invention.

EXAMPLE 1

A culture liquor was prepared in such a manner that 200 g of peeled potato slices were cooked with 1 liter of distilled water for 1 hour and the cooked mixture filtered with a cloth. To the filtered liquid mixture, were added 20 g of glucose, 1.5 g of yeast extract, 2.0 g of $KH_2PO_4$ and 0.5g of $MgSO_4.7H_2O$ and the mixture was increased to 1 liter with distilled water. Each 100 ml of this culture liquor were stored in a 500 ml Erlenmeyer flask and pasteurized by heating it at 121° C. for 20 minutes. Fungal cells of *Penicillium janthinellum* M5613 (FERM BP-1674) were inoculated from a preserved slant culture agar medium and the cultivation was effected at 28° C. for 4 days with shaking.

10 ml of the culture liquor wre removed and subjected to sonication at a frequency of 15 kHz at 3° C. for 20 minutes, in order to destroy the cells. This sonication was repeated 5 times to obtain 50 ml of crude enzyme solution (20 u). This crude solution was centrifuged at a rate of 15,000 r.p.m. at 5° C. for 20 minutes. The pH of the supernatant liquid was adjusted to 5.0 with 1 N hydrochloric acid and this solution was centrifuged again at a rate of 15,000 r.p.m. at 5° C. for 20 minutes. The precipitate was dissolved in 50 ml of 20 mM buffer solution (pH 6.5) of potassium salt of phosphate and the solution was then centrifuged at a rate of 15,000 r.p.m. for 20 minutes at 5° C. to obtain a supernatant liquid layer (11.3 u). 5 ml of this supernatant liquid was carried out on a column of Sephadex G-100 of 2.8×60 cm treated by a 20 mM potassium/phosphate buffer solution (pH 6.5) for pH adjustment. This gel filtration was repeated ten times to obtain 50 ml of an enzyme solution (7.2 u). 100 mg of sucrose were added to the enzyme solution and the solution was then subjected to a freeze-drying in a usual manner to obtain 320 g of a freeze-dried product.

EXAMPLE 2

Figure 6:
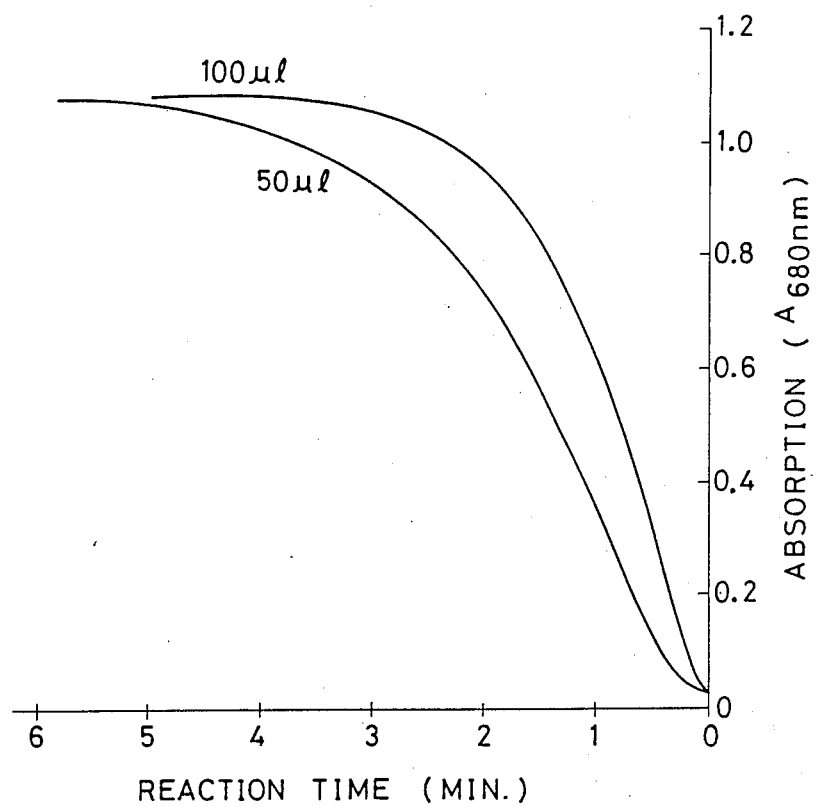
FIG. 6 depicts the variation of remaining bilirubin with time after commencement of the enzyme reaction using the bilirubin oxidase according to the invention.

3 ml of a substrate solution prepared in accordance with the method of preparation of a substrate solution described in connection with the determination of enzyme activity were placed in a 3 ml quartz cell and thereto added 30 μl of 10 nM $HgCl_2$ solution. Two reaction solutions were prepared by adding to the so obtained solution a bilirubin oxidase solution in an amount of 50 μl and of 100 μl respectively, which had been prepared by weighing accurately 50 μg of the freeze-dried bilirubin oxidase obtained in Example 1 and the so weighed bilirubin oxidase was dissolved in 6.5 ml of distilled water. Each of the so prepared reaction solution was then placed in a spectrophotometer (Model UV-210A of the firm Shimadzu Corporation) and the absorbancy at a wavelength of 680 nm was observed at 37° C. through the course of the reaction at various time intervals. The results are shown in FIG. 6 as a time chart, from which it is seen that the reaction of the bilirubin oxidase has been completed after 6 minutes from the start of the reaction in the case where 50 μl of the enzyme solution were used and that the reaction has been completed after 3.5 minutes in the case where 100 μl of the enzyme solution were used. It is apparent from these results that it is possible to carry out the determination of bilirubin content in a sample within a short period of time under such conditions by determining the amount of biliverdin produced and that it is also possible, with the bilirubin oxidase according to the invention, to remove bilirubin under circumstances in which little effect on substances other than bilirubin occurs, since the substrate specificity of the bilirubin oxidase to bilirubin is quite high.

EXAMPLE 3

Figure 7:
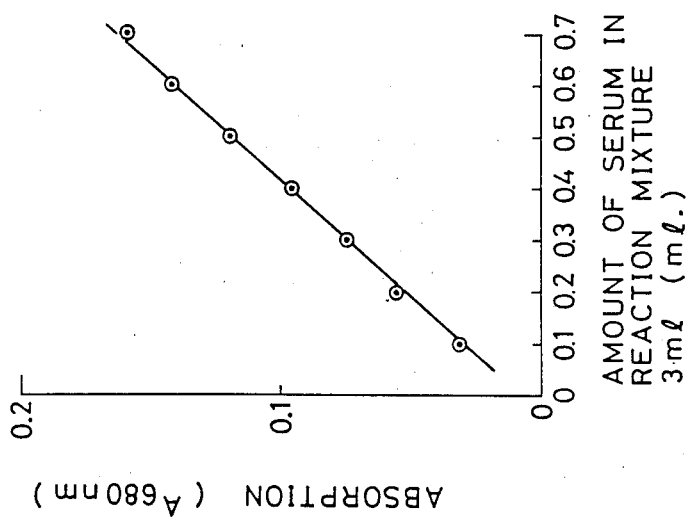
FIG. 7 confirms the linearity in the analysis of bilirubin concentration using the enzyme according to the invention observed for human serum.

A human serum was sampled in amounts of 0.1, 0.2, 0.3, 0.4, 0.5, 0.6 or 0.7 ml. Each of the samples was increased to 3 ml with 0.1M buffer solution of tris-hydrochloric acid and thereto added 0.1U of the bilirubin oxidase according to the invention, whereupon it was incubated at 37° C. for 30 minutes. The so-treated reaction liquor was then placed in a spectrophotometer (Model UV-210A of the firm Shimadzu Corp.) to determine the absorbancy at a wavelength of 680 nm at 37° C. The results are given in FIG. 7, which shows the linearity of the absorbancy versus the concentration of blood serum.

COMPARISON EXAMPLE

Preparation of Calibration Curve (1) Preparation of Enzyme Solution

For each determination, an enzyme test solution was prepared by adding to a buffer solution of 0.1M tris-hydrochloric acid (pH 8.4) the bilirubin oxidase according to the present invention in an amount of 0.1 U/test.

(2) Preparation of Standard Bilirubin Solution 5.9 mg of a standard product of non-conjugated and non-combined bilirubin supplied form the firm Wako Junyaku were weighed accurately and wetted with 0.5 ml of 5N solution of NaOH and then dissolved in 10 ml of 1N buffer solution (pH 5.4) of tris-hydrochloric acid, whereupon the solution was increased to 100 ml with distilled water. From ths solution, 100 μM bilirubin solution was prepared. This was diluted with 0.1M buffer solution (pH 8.4) of tris-hydrochloric acid to prepare standard bilirubin solutions in concentrations of 2, 4, 6, 8, 10 and 14 μM respectively.

(3) Calibration Curve

Figure 8:
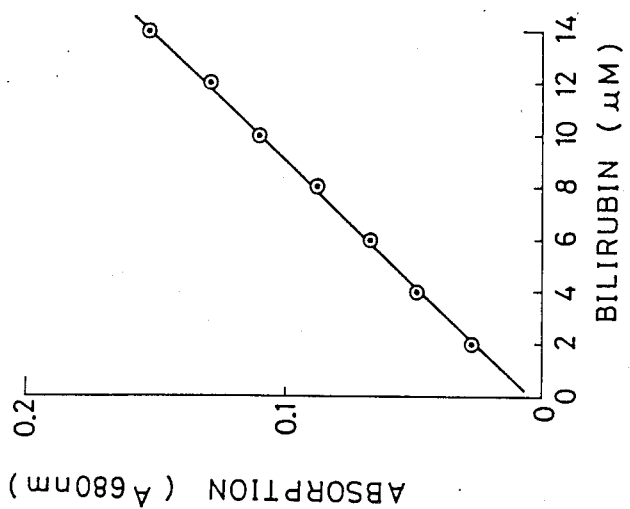
FIG. 8 shows the experimental results for preparing the calibration curve for analyzing bilirubin using the enzyme according to the present invention and a standard product of bilirubin.

To each 3 ml of the above solutions of standard bilirubin product was added the enzyme test solution mentioned above and the mixture was incubated at 37° C. for 30 minutes. Each reaction solution was examined for its light absorbancy on a spectrophotometer (Model UV-210A of the firm Shimadzu Corp.) at a wavelength of 680 nm at 37° C. The results are given in FIG. 8, which shows an excellent linearity of the absorbancy with the concentration of bilirubin.

The bilirubin oxidase according to the present invention has a marked substrate specificity to bilirubin to permit it to be used advantageously in the diagnosis of hepatic diseases and as well as for removing bilirubin from samples to be analyzed where the presence of bilirubin will inhibit such analysis. Due to the remarkable high level of enzyme activity, utilization in the decolorizing of biochemically treated water from, such as, activated sludge treatment of night soil etc. may also be expected.

What is claimed is:

1. A bilirubin oxidase possessing a substrate specificity for bilirubin but not to biliverdin, catechol and hemin, said bilirubin oxidase catalyzing the enzyme reaction between two moles of bilirubin and one mole of oxygen to yield two moles of biliverdin and two moles of water, said bilirubin oxidase being in purified form.

2. A bilirubin oxidase according to claim 1, which exhibits the following physiochemical properties:

| (a) Molecular weight | 500,000 ± 50,000 |
| (b) Isoelectric point | pH 4.7 ± 0.5 |
| (c) Km value | $1.1 \times 10^{-4} \pm 1 \times 10^{-5}$ M |
| (d) Optimum pH | 8.5–9.0 |
| (e) Stable pH range | from 4.0 to 4.5 |
| (f) Optimum temperature | 55 to 60° C. |
| (g) Heat stability | up to 50° C. |

3. A process for the production of bilirubin oxidase, comprising cultivating a bilirubin oxidase-producing fungus of the strain *Penicillium janthinellum* M 5613 deposited at the Institute of Microbiological Industry and Technology of the Agency of Industrial Science and Technology Japan under deposition No. FERM BP-1674.

4. In a method for determining the content of bilirubin in a sample to be analyzed, comprising contacting the sample with bilirubin oxidase to convert bilirubin in the sample into biliverdin and subsequently determining the amount of biliverdin formed or the amount of oxygen consumed, the improvement specificity for bilirubin oxidase possesses a substrate specificity for bilirubin but not to biliverdin, catechol and hemin, said bilirubin oxidase catalyzing the enzyme reaction between two moles of bilirubin and one mole of oxygen to yield two moles of biliverdin and two moles of water.

5. The method of claim 4, wherein said bilirubin oxidase exhibits the following physiochemical properties:

| | | |
|---|---|---|
| (a) | Molecular weight | $500,000 \pm 50,000$ |
| (b) | Isoelectric point | pH $4.7 \pm 0.5$ |
| (c) | Km value | $1.1 \times 10^{-4} \pm 1 \times 10^{-5}$ M |
| (d) | Optimum pH | 8.5–9.0 |
| (e) | Stable pH range | from 4.0 to 4.5 |
| (f) | Optimum temperature | 55 to 60° C. |
| (g) | Heat stability | up to 50° C. |

6. A method for eliminating bilirubin contained in a sample to be analyzed, comprising contacting the sample with a bilirubin oxidase having a substrate specificity for bilirubin but not to biliverdin, catechol and hemin and catalyzing the enzyme reaction between two moles of bilirubin and one mole of oxygen to yield two moles of biliverdin and two moles of water.

7. The method of claim 6, wherein said bilirubin oxidase exhibits the following physiochemical properties:

| | | |
|---|---|---|
| (a) | Molecular weight | $500,000 \pm 50,000$ |
| (b) | Isoelectric point | pH $4.7 \pm 0.5$ |
| (c) | Km value | $1.1 \times 10^{-4} \pm 1 \times 10^{-5}$ M |
| (d) | Optimum pH | 8.5–9.0 |
| (e) | Stable pH range | from 4.0 to 4.5 |
| (f) | Optimum temperature | 55 to 60° C. |
| (g) | Heat stability | up to 50° C. |

* * * * *